US00PP16660P3

(12) United States Plant Patent
Turner, Sr.

(10) Patent No.: US PP16,660 P3
(45) Date of Patent: Jun. 13, 2006

(54) *NERIUM OLEANDER* PLANT - TURNER'S 7-678

(50) Latin Name: *Nerium oleander*
Varietal Denomination: Turner's 7-678

(76) Inventor: Ted L. Turner, Sr., 6503 S. Padre Island Dr., Corpus Christi, TX (US) 78412

( * ) Notice: Subject to any disclaimer, the term of this patent is extended or adjusted under 35 U.S.C. 154(b) by 84 days.

(21) Appl. No.: 10/952,355

(22) Filed: Sep. 27, 2004

(65) Prior Publication Data

US 2006/0070151 P1 Mar. 30, 2006

(51) Int. Cl.
*A01H 5/00* (2006.01)

(52) U.S. Cl. ..... Plt./233

(58) Field of Classification Search ..... Plt./233
See application file for complete search history.

(56) References Cited

U.S. PATENT DOCUMENTS

PP6,339 P 10/1988 Turner, Sr.
PP7,619 P 8/1991 Turner, Sr.

*Primary Examiner*—Anne Marie Grunberg
*Assistant Examiner*—Annette H Para
(74) *Attorney, Agent, or Firm*—Stewart N. Rice

(57) ABSTRACT

A *Nerium oleander* plant which has a petite and upright and sprawling habit of growth, being particularly characterized by long blooming periods and the unique color of its inflorescence and its habit of growth, the flowers being a dusty rose color with areas of pale yellow in the corona or throat, and which flowers grow in cymes or clusters.

1 Drawing Sheet

Variety Name

The proposed variety name of my new plant is *Nerium oleander* 'Turner's 7-678'.

DESCRIPTION OF THE INVENTION

The present invention relates to a new and distinct variety, of petite size, of *Nerium oleander* which was originated by me as a seedling by selection and crossing. I crossed a *Nerium oleander* 'Turner's Carnival' with a *Nerium oleander* 'Turner's Tickled Pink'. The 'Turner's Carnival' is the subject of U.S. Plant Pat. No. 6,339 issued Oct. 18, 1988 to Ted L. Turner, Sr., and this plant is a petite size plant which produces flowers which are soft pink in color. 'Turner's Tickled Pink' is the subject of U.S. Plant Pat. No. 7,619 issued Aug. 13, 1991, to Ted L. Turner, Sr., and this plant is a petite size plant with flowers which are peach-pink in color. However, in making my crosses, I observed that polination could have been accomplished by bees from unknown plants. Thus unknown parentage could have been introduced by the bees even though I did not purposely introduce any parentage other than the 'Turner's Carnival' and 'Turner's Tickled Pink'. The *Nerium oleander* of my new variety differs from the 'Turner's Carnival' and the 'Turner's Tickled Pink' mentioned above mainly in the growth habit and color of the flowers. The growth habit of my new variety is wider and more sprawling than the 'Turner's Carnival' and the 'Turner's Tickled Pink'. The color of the flowers of my new variety is a dusty rose, while the flowers of the 'Turner's Carnival' are soft pink and those of the 'Turner's Tickled Pink' are peach-pink.

From the group of seedlings I observed a plant, being the plant claimed herein, having a new and distinct color of flowers, and from cuttings of such plant I was able to asexually reproduce plants having the same characteristics and flower color as the original seedling. The plant observed for this patent application had been grown in a greenhouse, was in a five gallon container, and was about three years old. All of the descendant plants showed the same characteristics as the original seedling, and as a result of extensive observations and tests which are not described in full herein for sake of brevity, it is my opinion and I am convinced that my new plant is a new variety of *Nerium oleander* which is distinguished from all other varieties of which I am aware as evidenced by the following unique combination of principal characteristics which are outstanding therein:

(1) An upright sprawling habit of growth and of petite size making it especially suitable for hedges and as a pot plant, or to add garden color;

(2) An ability to be asexually reproduced;

(3) An ability to flower substantially throughout the year with long continuous blooming periods;

(4) The ability to bloom in partial shade, such as morning sun only;

(5) The ability to be a good greenhouse bloomer and bloom year around in a greenhouse;

(6) The ability to initially grow and flower in relatively small pots as small as about eight centimeters in diameter although, the plant should be placed in a larger pot of at least 30 centimeters to obtain larger growth;

(7) The ability to produce a flower having a dusty rose color with areas of yellow in the corona;

(8) The ability to produce a plant having flowers arranged in cymes or clusters; and (9) The ability to grow in windy conditions.

Asexual reproductions of my new variety as by cuttings shown that the foregoing characteristics and distinctions come true to form and are established and transmitted through succeeding propagations. The ongoing planned breeding program which resulted in the plant described herein and the initial asexual reproduction of this plant have taken place in a nursery in Corpus Christi, Nueces County, Tex.

BRIEF DESCRIPTION OF THE DRAWING

The accompanying FIGURE is a photograph of a typical flower on the plant of my new variety more clearly illustrating the colors present on each flower. The true color of the foliage and flowers is described in the following description and is depicted in the FIGURE which depicts the color as nearly as true as is reasonably possible in a color illustration of this type.

The following is a detailed description of my new variety of *Nerium oleander*, which color numbers are in accordance with the Pantone Matching System of colors for printing inks, Pantone Color Formula Guide 747 XR, 1987–1988, published by Pantone, Inc. Terms used to describe colors are those of ordinary significance.

The Plant

Growth habit: Upright, sprawling, petite size; the height of an unpruned mature plant will be from about 1.5 to 2.5 meters, but has not yet been determined; fast growing in shady areas and slower in full sun. The plant grows full from ground level upward, with its width generally greater than its height, the width of the plant being about 110% to 150% of the height. The plant is about the same height but wider than the *Nerium oleander* 'Turner's Carnival' referenced above, and slightly smaller and more compact than the *Nerium oleander* 'Turner's Tickled Pink' referenced above.

Hardiness: Adapted to seaside planting as it tolerates soil with relatively high salt content; tolerates droughts; will not withstand prolonged and severe freezing weather; most suitable for the Southern United States from California to Florida, in the areas known as Zones 9 and 10; withstands heat and light and grows either in full sun or in partial shade (up to 50% shade) such as morning sun only; can be started and will bloom in small pots as small as about eight centimeters in diameter, although the plant should be transferred to a larger pot of 30 centimeters or larger to obtain a larger growth.

Branches: The plant is loosely branched from ground level with main branches and branchlets slightly drooping or sprawling. The plant does not develop a central leader or trunk. New growth of branches is a light to medium green, Color No. 390U, changing to light greenish brown in color, Color No. 125U, as branches mature. The old or matured wood is a pale brown, Color No. 456U.

Blooming period: Under outside conditions, blooms off and on substantially the entire year, being in bloom about 80% of the time. The plant will bloom substantially all the time in a greenhouse.

The Foliage

Type: Broadleaf evergreen; numerous; petioled; grow in a whorl with three leaves in each whorl.

Shape: Linear-lanceolate, with entire margins. Apex is more or less acuminate and slightly non-symmetrical, and base is acute.

Petioles: Length, from about 3 to 5 mm; color pale green, Color No. 586U.

Leaf size: Length of mature leaf from about 110 to 140 mm; width of mature leaf about 18 to 22 mm. Size of leaf varies according to sunshine conditions at the time the leaf is produced, with larger leaves being produced under cloudy conditions than under sunny conditions.

Venation: Midrib on under surface prominent and readily apparent and is pale green, Color No. 586U; on upper surface midrib is clearly visible and slightly recessed, and is pale green, Color No. 584U; lateral veins are not readily apparent on upper surface but under surface contains numerous, delicate, almost parallel lateral veins which are readily apparent, the lateral veins being substantially perpendicular to the midrib.

Leaf color: Mature leaves: upper surface — dark green, Color No. 575C; under surface lighter in color than upper surface, being a medium green, Color No. 5777U.

New leaves: About the same color as mature leaves, but slightly lighter and brighter in color than mature leaves.

Leaf texture: Tough, leathery; smooth; upper surface — non-glossy; lower surface — dull.

The Inflorescence

Position and abundance: Flowers cluster at twig or branch ends in terminal cymes, with cymes appearing at various positions from the lower part to the upper part of the plant. Each cyme is tightly clustered with generally about 8 to 12 flowers each, although some cymes may contain more or less flowers.

Form: Single, regular; pediceled; petals united in a sympetalous corolla; salverform; tube spreads into five limbs or lobes; each flower is about 40 to 45 mm across; corona conspicuous at junction of tube and spreading limb, corona about 10 to 12 mm in diameter and a depth of about 12 mm which is much shorter than spreading limbs, the corona having five crownlike appendages, each appendage corresponding to a limb, most appendages being 4 toothed at their outer ends.

Buds: Limbs convolute in the bud, obliquely apiculate, the folds twisting counterclockwise when viewing down onto the tip of the bud, such the limbs of the flower twist slightly clockwise when viewing down into the flower.

Calyx: Of 5 persistent sepals, imbricate in the bud, lanceolate, acuminate, about 5 mm long. The sepals have a relatively smooth surface texture. The calyx and sepals are light green, Color No. 372U.

Stamen: 5 stamens; filaments partly adnate to corolla tube; anthers with 2 basal tails, apex long-attenuate, hairy. The stamens are about 10 mm in length, with a medium yellow color, Color No. 121C.

Pistil: The style portion of the pistil is white in color with the outer end or stigma portion being a pale yellow color, and with the pistil being approximately 15 mm in length.

Color of flower: Limbs or petals of the corolla in new flowers are a dusty rose color, Color No. 204U. As is the case with most oleanders, blooms produced under a full sun may be lighter in shade than those produced on cloudy days. The corona is pale yellow, being a pale version of Color No. 127U. The outside of the corolla tube of each flower is a dark pink, Color No. 191U with areas of golden yellow, Color No. 120U.

Fragrance: The flowers have no appreciable fragrance.

Color of buds: Dark rose, Color No. 206U.

To further describe my new variety of *Nerium oleander*, it is very similar in height to the other well-known petite size *Nerium oleanders* which grow in an upright manner, except for the color of the flowers, and except that my new variety appears to be wider and more sprawling in growth habit. I am not aware of any *Nerium oleander* of a petite size having a flower and growth habit which is the same as that produced by my plant.

I claim:

1. A new and distinct variety of petite size *Nerium oleander* plant substantially as shown and described, having an upright and sprawling habit of growth making it especially suitable for hedges, having an ability to be asexually reproduced, having the ability to flower off and on throughout the entire year with long continuous blooming periods, having the ability to grow in full sun or in partial shade, being an excellent greenhouse plant, and being particularly characterized by its petite size combined with the unique color of its inflorescence and its growth habit, and having terminal cymes of flowers which are a dusty rose color with throats or coronas of a pale yellow.

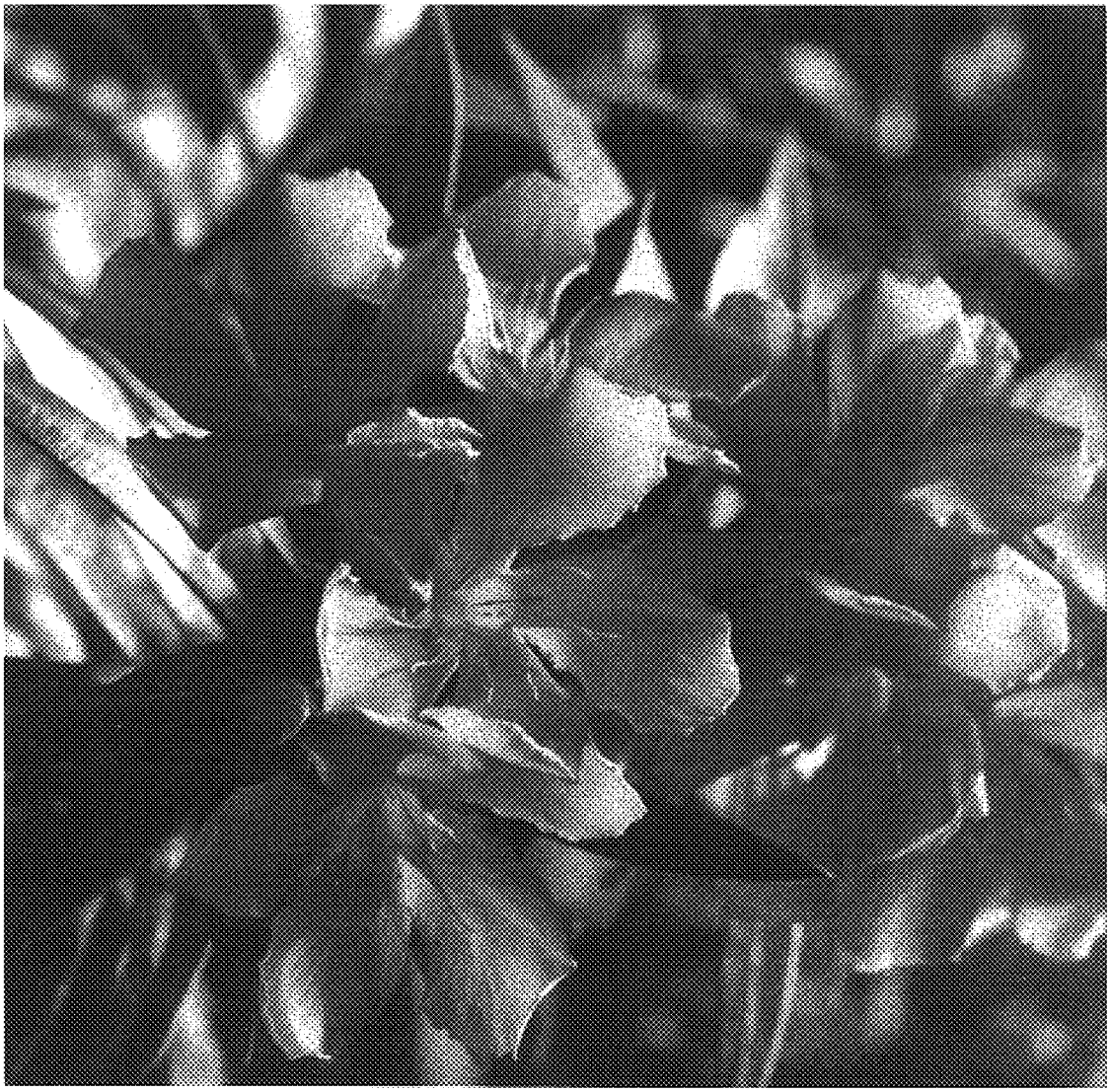

* * * * *